(12) United States Patent
Torkildsen

(10) Patent No.: US 6,802,204 B1
(45) Date of Patent: Oct. 12, 2004

(54) ARRANGEMENT FOR IMPROVED WATER-OIL RATIO MEASUREMENTS

(75) Inventor: Bernt Helge Torkildsen, Bergen-Sandviken (NO)

(73) Assignee: Framo Engineering AS, Sandsli (NO)

( * ) Notice: Subject to any disclaimer, the term of this patent is extended or adjusted under 35 U.S.C. 154(b) by 0 days.

(21) Appl. No.: 09/959,555

(22) PCT Filed: Apr. 28, 2000

(86) PCT No.: PCT/GB00/01660

§ 371 (c)(1),
(2), (4) Date: Jan. 18, 2002

(87) PCT Pub. No.: WO00/67018

PCT Pub. Date: Nov. 9, 2000

(30) Foreign Application Priority Data

Apr. 30, 1999 (GB) .............................. 9910160

(51) Int. Cl.⁷ .............................................. G01N 37/00
(52) U.S. Cl. .................................................... 73/61.44
(58) Field of Search ............................. 73/61.44, 1.02, 73/861.04

(56) References Cited

U.S. PATENT DOCUMENTS

| | | | | |
|---|---|---|---|---|
| 4,773,257 A | * | 9/1988 | Aslesen et al. | 73/61.44 |
| 5,135,684 A | | 8/1992 | Mohn et al. | |
| 5,962,780 A | * | 10/1999 | Prouvost | 73/198 |
| 6,032,539 A | * | 3/2000 | Liu et al. | 73/861.04 |
| 6,128,962 A | * | 10/2000 | Marrelli et al. | 73/861.04 |
| 6,155,102 A | * | 12/2000 | Toma et al. | 73/61.44 |
| 6,182,505 B1 | * | 2/2001 | Segeral | 73/61.44 |
| 6,234,030 B1 | * | 5/2001 | Butler | 73/861.04 |

FOREIGN PATENT DOCUMENTS

| | | | |
|---|---|---|---|
| GB | 2 319 620 | | 5/1998 |
| WO | WO 99/05482 | | 2/1999 |
| WO | WO 91/02948 | * | 8/1999 |

OTHER PUBLICATIONS

R. Thorn et al., "Recent Developments in Three–Phase Flow Measurement", *Measurement Science and Technology*, GB, IOP Publishing, Bristol, vol. 8, No. 7, Jul. 1, 1997, pp. 0957–0233.

* cited by examiner

*Primary Examiner*—Michael Cygan
(74) *Attorney, Agent, or Firm*—Young & Thompson

(57) ABSTRACT

A method of, and apparatus for measuring the relative proportions of oil and water in a flowing multiphase fluid includes allowing the gas, oil and water phases of the multiphase fluid at least partially to separate, diverting at least some of the separated gas phase from the flowing fluid, into a bypass conduit, through a separating module, such as the tank of a homogenizing unit, where the gas phase tends to separate and collect above a pool of fluid, and measuring the relative proportions of oil and water in the undiverted fluid. A valve is located in the bypass conduit which has an inlet leading from the upper section of the tank (where gas collects) and an outlet joining the outlet pipe leading from the homogenizing unit downstream of metering apparatus.

19 Claims, 1 Drawing Sheet

ARRANGEMENT FOR IMPROVED WATER-OIL RATIO MEASUREMENTS

BACKGROUND OF THE INVENTION

The present invention relates to apparatus and method for fluid measurement and is particularly applicable to the measurement of individual proportions of the component phases of a multiphase fluid.

It is particularly useful in the field of fluid flow from oil and gas wells. The fluid flowing from a well generally comprises a mixture of oil, gas and water and it can be of great advantage to measure the individual phases without first having to separate them.

DESCRIPTION OF THE RELATED ACT

This has been done using apparatus as disclosed in EP-A-0424 503. The relative amount of water and oil is often critical but unfortunately inherently difficult to measure accurately when there is a large amount of gas in the mixture.

SUMMARY OF THE INVENTION

The present invention seeks to improve the accuracy of fluid flow measurements.

According to the present invention there is provided a method of measuring the relative proportions of oil and water in a flowing multiphase fluid, the method comprising allowing the gas, oil and water phases of the multiphase fluid at least partially to separate, diverting at least some of the separated gas phase from the flowing fluid, into a bypass conduit, measuring the relative proportions of oil and water in the undiverted fluid.

Preferably the multiphase fluid is directed to flow through a separating module wherein the gas phase tends to separate and collect above a pool of fluid.

In a particularly preferred embodiment such a separating module comprises the tank of a homogenising unit. Such as is described in EP-A-0 379 319. The bypass conduit is then constructed with an inlet leading from the upper section of the tank (where gas collects) and an outlet joining the outlet pipe leading from the homogeniser, downstream of metering apparatus. A valve is located in the bypass conduit.

The valve may be manually or automatically operated, for example based on a pre-programmed metering cycle. The valve may be a choke or alternatively arranged to allow a flow rate for the bypassing gas phase appropriate to the pressure drop monitored by the multiphase flow meter located in the outlet pipe from the homogenising unit.

The valve will be kept closed for normal operation, but will be opened periodically for the performance of high quality water-oil ratio measurements. Normally the water-oil ratio does not vary dramatically over short periods of time. The high quality measurement made using the method of the present invention can be compared to normal measurements for improved accuracy or to update calibration values or parameters.

The valve may also be remotely operated.

The method of the invention also allows in-situ sensor calibration operations to be performed. This is particularly useful for example for sub-sea applications and other permanent installations where there is an unknown mixture in the meter, so that calibration was hitherto very difficult.

Using the method of the invention, calibration can be effected at two different conditions, such as two different gas volume fractions, for the same production conditions.

No measurement of the fluid in the bypass conduit is necessary and it is not necessary to ensure that only the gas phase is diverted; spillover of liquid phase will not affect operation of the invention.

Apparatus for performing the method is also provided.

Thus the invention provides a very versatile method of increasing the accuracy of fluid flow measurements on multiphase fluids.

BRIEF DESCRIPTION OF THE DRAWINGS

For a better understanding of the present invention and to show how the same may be carried into effect, reference will now be made to the accompanying drawings in which.

DESCRIPTION OF THE PREFERRED EMBODIMENTS

Figure 1:
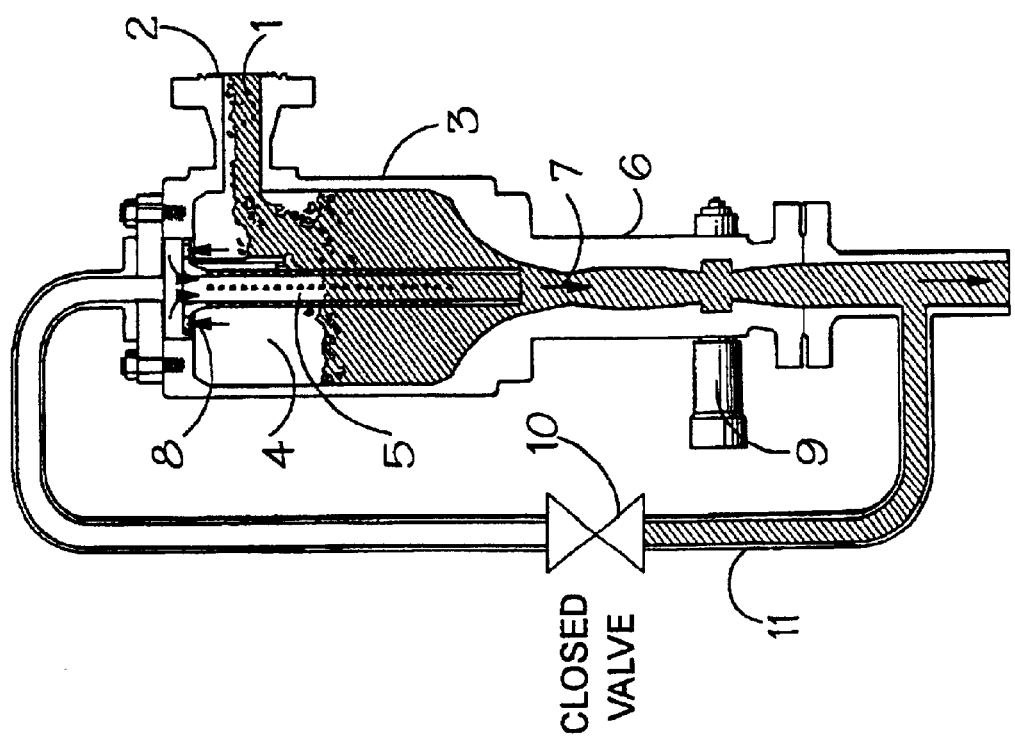
FIG. 1 is a cross-sectional view of apparatus embodying the invention with a closed valve.

FIG. 1 illustrates the normal mode of operation of the apparatus. Multiphase fluid 1 enters through inlet conduit 2 and partially fills a chamber 3. The fluid 1 has a tendency to separate as it enters and in chamber 3 a gaseous phase occupies the volume 4 of chamber 3 and lies above the fluid 1.

A perforated pipe 5 is positioned generally in the centre of chamber 3 and is coaxial with it. This arrangement serves to assist homogenisation of the multiphase fluid. The liquid phase in the bottom of chamber 3 enters pipe 5 through the lower perforations and also flows out of chamber 3 directly through outlet pipe 6 in which a restriction or venturi 7 is positioned. The gaseous phase lying above the liquid phase is drawn into the top of the pipe 5 as shown by arrows 8 and also through the upper perforations of the pipe 5 by the suction effect created by the flowing fluid phase particularly by the venturi effect in the restriction 7.

A meter 9 in the outlet conduit 6 measures flow rates and proportions of oil to water in the out-flowing fluid. With valve 10 closed there is no flow of gas or liquid or any combination, through bypass pipe 11.

Figure 2:
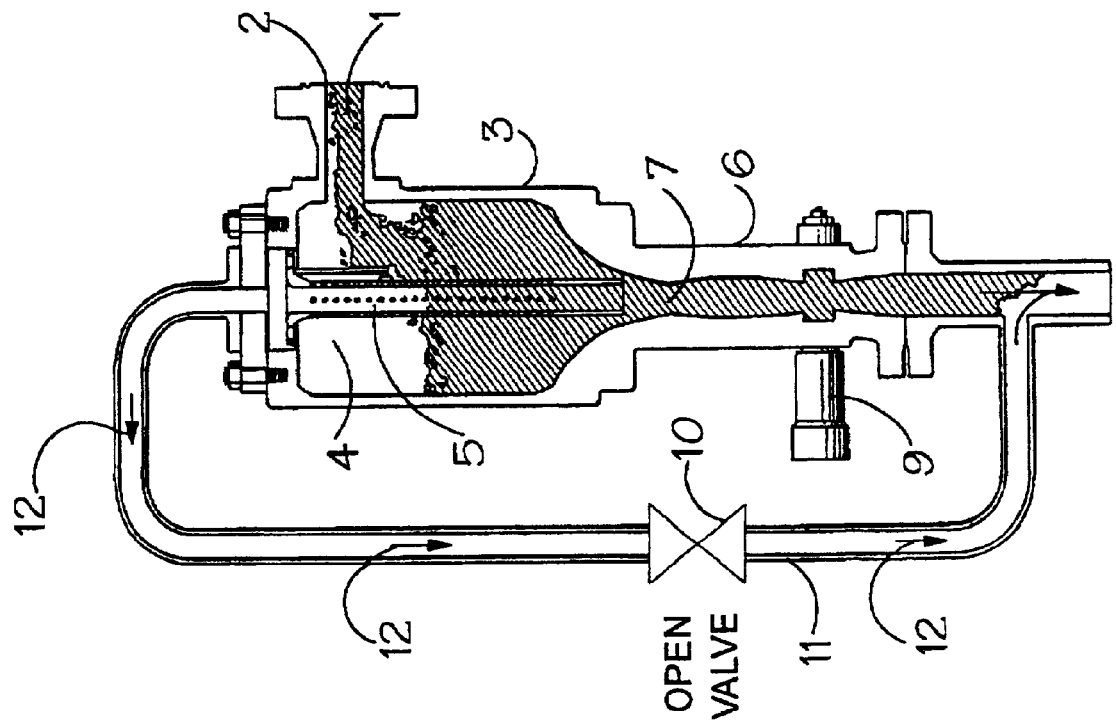
FIG. 2 is a cross-sectional view of apparatus embodying the invention with an open valve.

However as shown in FIG. 2, under certain circumstances the valve 10 is opened, allowing gaseous phase to flow through the bypass pipe 11 as shown by arrows 12. Thus less gaseous phase is present in the fluid flowing through meter 9 and the measurements of proportions of oil to water will be inherently more accurate than hitherto possible.

In many practical applications the gas phase may account for 95% or more of the multiphase mixture. Consider for example a meter with an inherent error margin of ±0.5%. If the water-oil ratio is measured at 3:1 and the gas is 96% the meter inherent inaccuracy means that the oil component (which accounts for only 1% of the total mixture) will be measured with a relative uncertainty of ±50% which is evidently somewhat unsatisfactory.

The present invention allows the proportion of gas in the mixture to be reduced temporarily and continuously while a measurement is made and to be re-introduced into the fluid flowing through the apparatus after the measurement is made.

Thus for example, the gas phase may be reduced, via the bypass, to 60%. If the water-oil ratio is again measured at 3:1 then this time the oil is 10% of the total and thus with an inherent meter error margin of ±0.5% the oil component will be measured with a relative uncertainty of 5%.

Evidently better accuracies are achieved if the gas is reduced more.

The opening times and durations of valve 10 may be controlled directly or in response to signals from the meter 9 or alternatively manually.

The meter 9 may be a composition meter such as the known dual energy gamma meter or the known total flow rate or momentum flux meter such as a venturi meter.

What is claimed is:

1. A method of measuring the relative proportions of oil and water in a flowing multiphase fluid, the method comprising the steps of:

passing the multiphase fluid through a homogenizing apparatus in such a way that the multiphase fluid forms a pool and a portion of the gas phase is allowed to separate from the multiphase fluid and collect above the pool, the homogenizing apparatus including a chamber for in which the pool forms, and a perforated pipe positioned in the chamber through which pipe the portion of gas phase is drawn to assist in the homogenization;

discharging multiphase fluid from the pool through an outlet pipe and through a metering apparatus;

diverting the portion of the gas phase into a bypass conduit to bypass the metering apparatus; and reintroducing the portion of the gas phase into the multiphase fluid downstream of the metering apparatus.

2. A method according to claim 1 wherein the bypass conduit comprises an inlet leading from the upper section of the tank, where gas collects, and an outlet joining the outlet pipe leading from the homogenizing apparatus.

3. A method according to claim 1 wherein a valve is located in the bypass conduit.

4. A method according to claim 3 wherein the valve is manually operated.

5. A method according to claim 3 wherein the valve is automatically operated.

6. A method according to claim 5 wherein the valve is operated depending on a pre-programmed metering cycle.

7. A method according to claim 3, wherein the valve is a choke.

8. A method according to claim 3, wherein the valve is arranged to allow a flow rate for the bypassing gas phase appropriate to the pressure drop monitored by the multiphase flow meter located in the outlet pipe from the homogenizing apparatus.

9. A method according to claim 3 wherein the valve is kept closed for normal operation.

10. A method according to claim 3 wherein the valve is remotely operated.

11. A method according to claim 1 when used for in-situ sensor calibration operations.

12. A method according to claim 1 when used for calibration at two different conditions for the same production conditions.

13. A method according to claim 12 when the two different conditions comprise two different gas volume fractions.

14. Apparatus for performing the method of claim 1.

15. Method of claim 1, wherein, the chamber has a first cross sectional area; and the outlet pipe has a second cross sectional area, the second cross sectional area being smaller than the first cross sectional area.

16. Apparatus for measuring the relative proportions of oil and water in a flowing multiphase fluid comprising an oil phase, a water phase and a gas phase, the apparatus comprising:

a homogenizing unit having a separating tank having a chamber adapted to allow a pool of the fluid to collect in said chamber and to allow a portion of the gas phase to separate and collect above the pool of fluid;

a perforated pipe positioned in the chamber through which perforated pipe the portion of gas phase is drawn;

a metering apparatus arranged to measure the relative proportions of the oil phase and the water phase in the multiphase fluid downstream of said tank; and a bypass conduit arranged to divert at least a part of the portion of the gas phase from above the pool within said tank and to reintroduce the part of the portion of the gas phase into the multiphase fluid downstream of the metering apparatus.

17. Apparatus according to claim 16 wherein the bypass conduit comprises an upper section where gas collects, an inlet leading from the upper section and an outlet which joins an outlet of the homogenizing apparatus.

18. Apparatus according to claim 16 wherein the bypass conduit further comprises a valve.

19. Apparatus according to claim 16 wherein, the chamber has a first cross sectional area;

the chamber is connected to an outlet pipe providing a path for the multiphase fluid to the metering apparatus;

the outlet pipe has a second cross sectional area, the second cross sectional area being smaller than the first cross sectional area.

* * * * *